United States Patent
Norman et al.

(10) Patent No.: US 10,183,126 B1
(45) Date of Patent: Jan. 22, 2019

(54) HEATED PATIENT TUBE ASSEMBLY

(71) Applicants: Scott Norman, Stillwell, KS (US);
Mark Petheram, Overland Park, KS (US); Anthony Hash, Olathe, KS (US)

(72) Inventors: Scott Norman, Stillwell, KS (US);
Mark Petheram, Overland Park, KS (US); Anthony Hash, Olathe, KS (US)

( * ) Notice: Subject to any disclaimer, the term of this patent is extended or adjusted under 35 U.S.C. 154(b) by 0 days.

(21) Appl. No.: 15/661,856

(22) Filed: Jul. 27, 2017

(51) Int. Cl.
*A61M 5/44* (2006.01)
*A61M 39/10* (2006.01)
*A61M 5/142* (2006.01)

(52) U.S. Cl.
CPC .............. *A61M 5/44* (2013.01); *A61M 5/142* (2013.01); *A61M 39/10* (2013.01); *A61M 2039/1022* (2013.01); *A61M 2205/0233* (2013.01); *A61M 2205/0244* (2013.01); *A61M 2205/18* (2013.01); *A61M 2205/3368* (2013.01); *A61M 2205/3592* (2013.01); *A61M 2205/3653* (2013.01); *A61M 2205/6081* (2013.01)

(58) Field of Classification Search
CPC ........ A61M 5/44; A61M 39/10; A61M 5/142; A61M 2205/3368; A61M 2205/3592; A61M 2205/6081; A61M 2205/18; A61M 2205/0244; A61M 2039/1022; A61M 2205/3653; A61M 2205/0233
See application file for complete search history.

(56) References Cited

U.S. PATENT DOCUMENTS

| | | | |
|---|---|---|---|
| 6,424,869 B1* | 7/2002 | Carr ..................... | A61B 18/18 607/101 |
| 9,211,381 B2* | 12/2015 | Faries .................... | A61M 5/44 |
| 2007/0088263 A1* | 4/2007 | Noice .................... | A61M 5/14 604/113 |
| 2009/0149811 A1* | 6/2009 | Thiebaud ................ | A61M 5/44 604/114 |
| 2013/0060185 A1* | 3/2013 | Lee ....................... | A61M 1/3693 604/6.08 |
| 2013/0122321 A1 | 5/2013 | Karandikar et al. | |
| 2015/0272654 A1 | 10/2015 | Esch et al. | |
| 2016/0330866 A1 | 11/2016 | Chi | |

FOREIGN PATENT DOCUMENTS

WO 2006097765 A1 9/2006

OTHER PUBLICATIONS

International Search Report and Written Opinion on PCT Appln. No. PCT/US2018/042999; Intl. Filing Date Jul. 20, 2018 and all references cited therein.

* cited by examiner

Primary Examiner — Lauren P Farrar
(74) Attorney, Agent, or Firm — Hovey Williams LLP

(57) ABSTRACT

A heated patient tube assembly that carries and warms fluids to a desired temperature includes an elongated hollow tube and a heating assembly at least partially embedded within the tube for heating the tube and fluids carried in the tube. The heated patient tube assembly can be selectively used in any combination of three different modes: a first mode in which the heating assembly is connected to a control assembly, a second mode in which the heating assembly is powered wirelessly, and a third mode in which the tube is inserted into and heated by an external warming device.

16 Claims, 6 Drawing Sheets

HEATED PATIENT TUBE ASSEMBLY

BACKGROUND

Intravenous (IV) tubes, enteral feeding tubes, blood transfusion tubes, and other fluid-carrying tubes are often used to deliver IV fluids, milk, feeding formulas, blood, and other fluids to infants, elderly person, and other patients. Because these fluids are often collected in advance and refrigerated, they must be warmed before given to patients.

Fluid warming assemblies have been developed for this purpose. One conventional type of fluid warming assembly includes a heated enclosure through which a fluid tube is threaded so that fluids in the tube are heated as they pass through the heated enclosure. However, conventional heated enclosures are configured for use with fluid tubes of specific diameters, thus making them un-usable with different sized tubes. Fluid tubes of different sizes and purposes are often used in short order, with each tube requiring a different model or type of heated enclosure. This significantly complicates patient care and increases the risk of incompatible fluid warming assembly components being used, which may result in fluids being under or over-heated when delivered to patients.

SUMMARY

The present invention solves the above-described problems and provides a distinct advance in the art of warming devices for IV fluids, feeding fluids, and other fluids delivered to patients. More particularly, the invention provides a versatile heated patient tube assembly that can be used to warm nearly any patient fluids without the need for multiple different heating devices.

A heated patient tube assembly constructed in accordance with an embodiment of the present invention broadly comprises an elongated hollow tube for carrying fluids to a patient; a heating assembly at least partially embedded within the tube for heating the tube and fluids carried in the tube; and a sensor for sensing a temperature of the fluids as they pass through the tube.

The tube may be an intravenous (IV) tube, an enteral feeding tube, a blood transfusion tube, and/or any other device configured to carry IV fluids, milk, feeding formulas, blood, and/or any other fluids to infants, elderly person, or any other patients or persons. The tube may be any length, diameter, and thickness for heating different fluids at desired temperatures.

The heating assembly heats fluids carried in the tube as they are delivered to a patient and comprises a heating element and a connector. The heating element is embedded in the tube substantially between the tube's inner and outer walls or integrated on the outer wall of the tube. The heating element produces resistive-type heat when subjected to an electrical current or electromagnetic wave to warm the tube and may be a metal wire, filament, flexible ceramic strip, etched foil heater, silicone particle, or any other element that generates heat.

The connector is coupled with the heating element and extends at least partially from the outer wall of the tube so that it may be connected to a control assembly or power source for powering the heating element. The connector may be a USB connector, mini USB connector, 4-pin or 16-pin connector, 120 VAC connector, 12 VDC connector, or any other connector capable of providing electricity to the heating element. The heating element may also receive power inductively or through other wireless methods. The heated patient tube assembly may include an RF antenna embedded in or attached to the tube for wirelessly controlling the heating element and receiving temperature readings, power usage, tube identifying information, and other data from the heated patient tube assembly.

The temperature sensor senses a temperature of the tube, fluid carried in the tube, or the heating element itself and may be a thermistor, thermocouple, silicon bandgap temperature sensor, or any other temperature sensor. The temperature sensor may be positioned anywhere on, in, or near the tube. In one embodiment, the temperature sensor is integrated with the heating element for obtaining a more accurate temperature reading. In another embodiment, the temperature sensor is a secondary wire or a thermistor attached to a secondary wire embedded in the tube. The temperature sensor may be coupled with a controller of a control assembly via the connector or may wirelessly send data to the controller.

In accordance with an important aspect of the invention, the heated patient tube assembly may be selectively used in any combination of three different modes: a first mode in which the heating element is powered or activated via the connector; a second mode in which the heating element is powered via induction; and a third mode in which the tube is inserted into and heated by an external warming device.

In the first mode, the connector is coupled with the control assembly. A user then activates the heating element via inputs on the control assembly. The heating element then begins to warm the fluid-carrying tube and fluids carried by the tube while the fluids are being delivered to a patient. The controller of the control assembly maintains the temperature of the fluids passing through the tube between approximately 90° F. (32° C.) and 103° F. (39° C.). Temperatures within this thermal-neutral zone (TNZ) are ideal for fluid adsorption and digestion. When the controller determines via the temperature sensor that the fluid temperature is above an upper threshold temperature, it temporarily deactivates or reduces the output of the heating element of the tube until the temperature has dropped below the upper threshold temperature. The controller may shut down and/or generate a warning if the temperature of the tube or fluid approaches, reaches, or surpasses 120° F. because temperatures at that level damage the tube and can be harmful to the patient.

In the second mode, the connector is left un-connected while the tube is positioned near or adjacent to an induction power source. The heating element then warms the fluid-carrying tube and fluids carried by the tube via a resistive current induced in the heating element by the induction power source. The temperature of the fluids passing through the tube may be maintained via the controller of the control assembly (or another suitable device) according to temperature signals transmitted by the RF antenna or other wireless means.

In the third mode, at least a portion of the tube is inserted into a fluid warming device and heated by a heating element of the fluid warming device. The temperature of the fluids passing through the tube may be maintained via a controller of the fluid warming device.

Importantly, more than one mode or aspects of more than one mode may be used simultaneously. For example, the connector may be coupled to the control assembly for collecting or displaying temperature data and other information, while the heating element is powered via an induction power source. Alternatively, the heated patient tube assembly may be powered via the connector while temperature data and other information is transmitted to the controller of the control assembly wirelessly via the RF antenna.

In some instances, supplemental heat or power may be desired and provided from two or more sources. For example, the connector may be coupled to the control assembly and the tube may be inserted into an external warming device such that the fluids are warmed via heat generated by the heating element and heat generated by the external warming device. This may be useful when the tube does not precisely fit the available external warming device and thus is not adequately heated by the external warming device. In a similar example, the first end of the tube is inserted into the external warming device such that it provides initial heat for warming the fluids to a temperature in the TNZ while the heating element of the tube maintains the temperature of the fluids as they pass through the tube.

The above-described heated patient tube assembly provides several advantages. For example, the heated patient tube assembly can be selectively operated in any combination of three different modes: the first mode in which the connector is connected to a control assembly, the second mode in which the heated patient tube assembly is powered wirelessly, and the third mode in which the tube is inserted into an external fluid warming device. More than one mode or aspects of more than one mode can be implemented simultaneously, which allows the heated patient tube assembly to be used with a wide variety of control assemblies, heating devices, and power sources. This significantly reduces the risk that the heated patient tube assembly is used with incompatible components and thus does not properly heat the fluids.

Another embodiment of the invention is a heated patient tube assembly broadly comprising an elongated hollow tube embedded with a number of thermally conductive particles and color changing particles. The thermally conductive particles produce resistive-type heat when subjected to an electrical current or electromagnetic wave and may be silicone, foil, copper, titanium, silver or other metal particles, or any other particles that transfer heat or generate heat under electric load. The thermally conductive particles may be microparticles or even nanoparticles and may be layered or extruded between inner and outer walls of the tube. Furthermore, the thermally conductive particles may be concentrated near the inner wall such that heat is transferred primarily inwardly towards the fluids in the tube. Similarly, the thermally conductive particles may be evenly dispersed along the tube or may be concentrated near the ends of the tube for warming the fluids as they enter the tube and maintaining their temperature before they exit the fluid passageway at the second end. The color changing particles indicate whether the temperature of the tube is within a safe or desired range and are embedded in the tube substantially between the tube's inner and outer walls. For example, the color changing particles may change colors to indicate that the temperature of the tube is between 98° F. and 105° F. and may change colors again to indicate that the temperature of the tube is near or over 120° F. and that the tube should be discarded. The color changing particles may be any thermochromic material such as an ink, a dye, crystals, or fabric. In another embodiment, a band, tape, wrap, or other strip of color changing material may be positioned on or attached to the outer wall of the tube.

The above-described heated patient tube assembly provides several advantages. For example, the thermally conductive particles can be layered or extruded in the tube and provide a more predictable and controllable heating profile along the tube. The thermally conductive particles may also be concentrated near an inner wall of the tube, thus providing more efficient heat transfer to the fluids as they pass through the tube. The color changing particles indicate when or if the tube should be discarded due to high heat.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

The drawing figures do not limit the invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning now to FIGS. 1-8, a heated patient tube assembly 10 constructed in accordance with an embodiment of the invention is illustrated. The patient tube assembly 10 broadly comprises an elongated hollow tube 12, a heating assembly 14, and a temperature sensor 16.

Figures 1, 2:
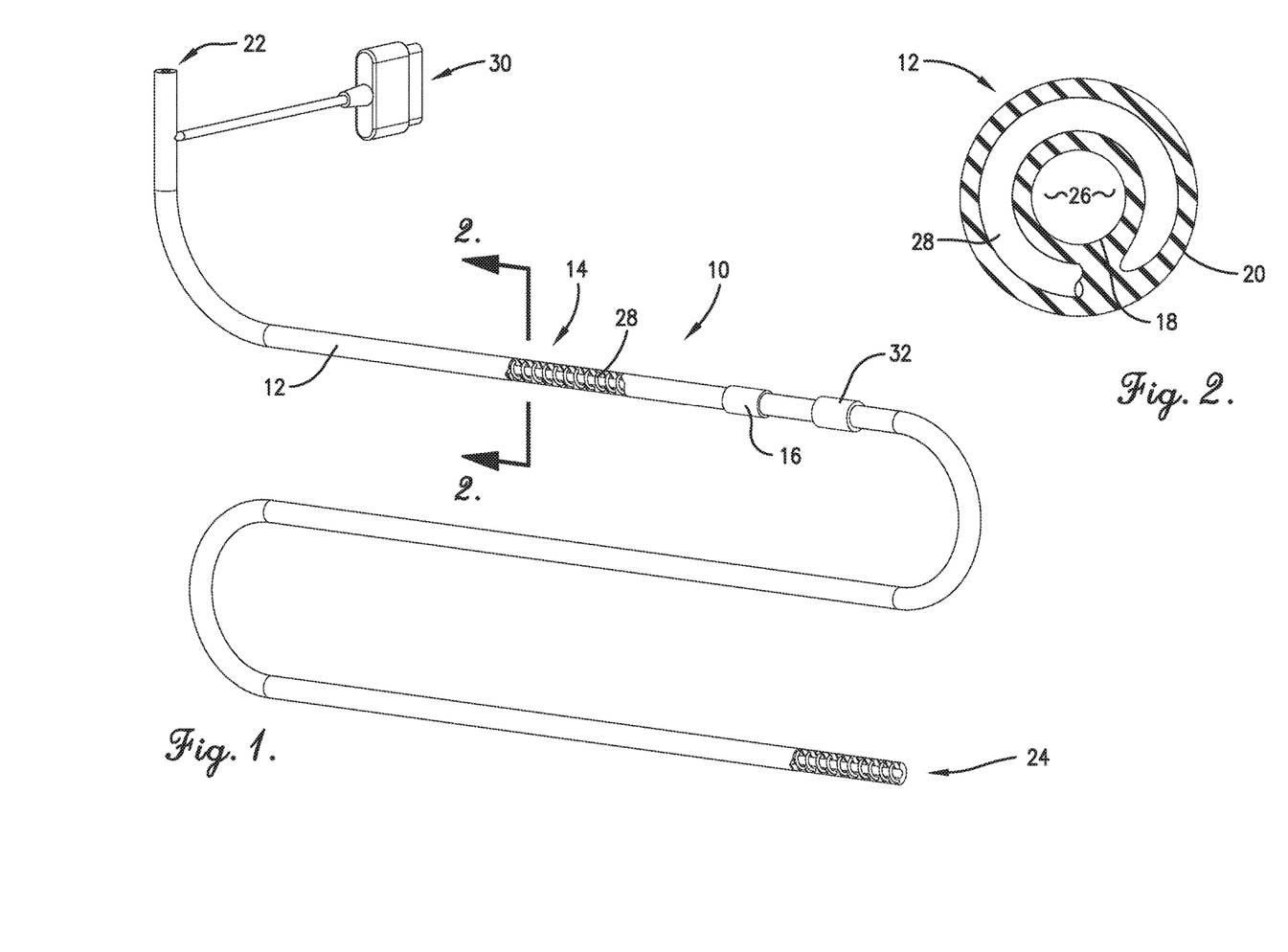
FIG. 1 is a perspective view of a heated patient tube assembly constructed in accordance with an embodiment of the invention with portions of the assembly shown in partial section to reveal internal components.
FIG. 2 is a vertical sectional view of the heated patient tube assembly of FIG. 1.

The tube 12 may be configured for use as an intravenous (IV) tube, an enteral feeding tube, a blood transfusion tube, and/or any other device for carrying IV fluids, milk, feeding formulas, blood, and/or any other fluids to infants, elderly person, or any other patients or persons. The tube 12 has an inner wall 18, an outer wall 20, and first and second open ends 22, 24, with the inner wall 18 defining an interior fluid passageway 26 for carrying fluids. The first open end 22 receives fluids from a pump, bag, or other fluid source and the second open end 24 delivers the fluids to a patient, or vice versa. The tube 12 may have any length and diameter and is preferably constructed of medical grade rubber, plastic, or similar flexible materials.

Figures 3, 4, 5:
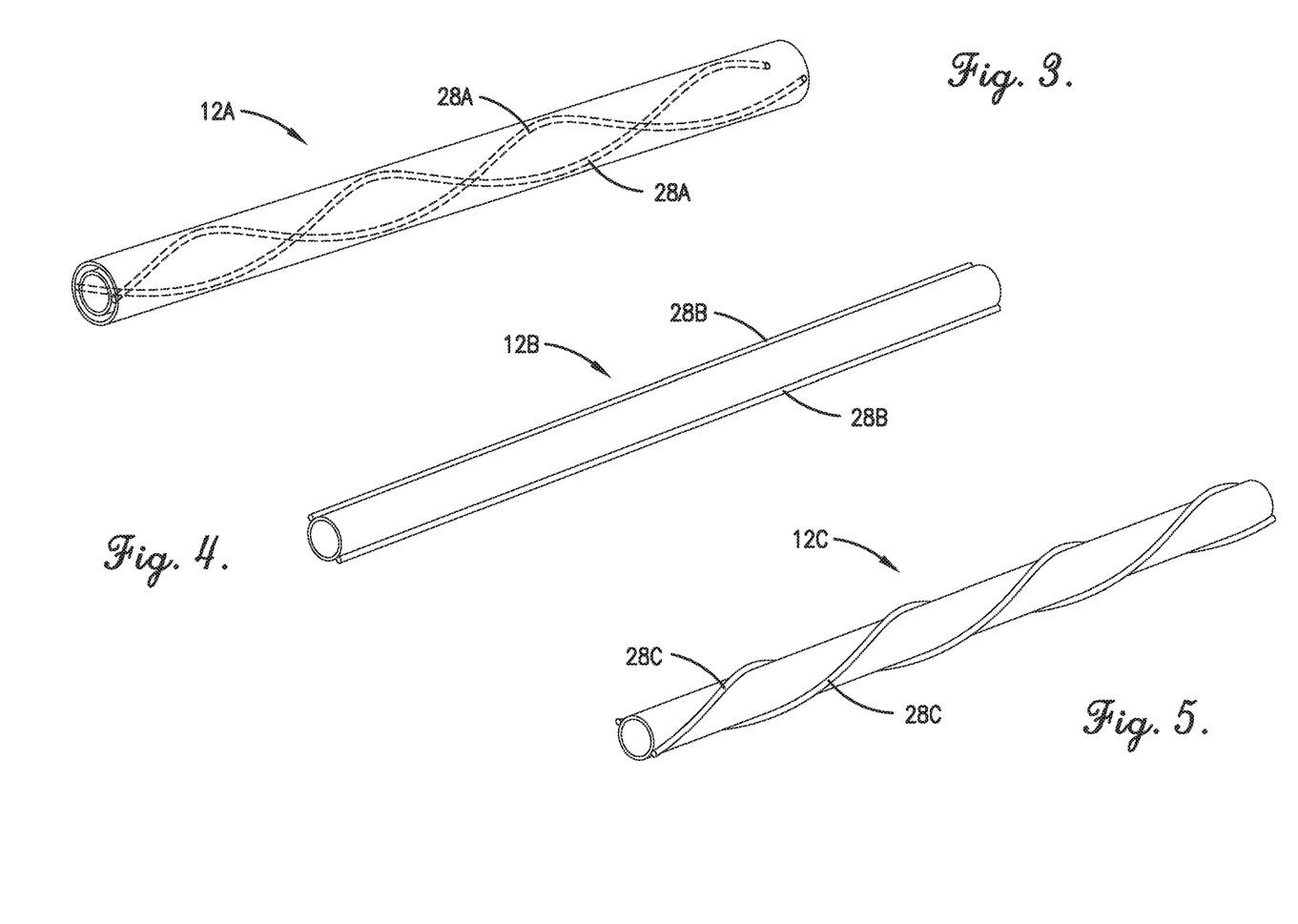
FIG. 3 is a perspective view of a portion of a heated patient tube showing a helical heating element embedded therein.
FIG. 4 is a perspective view of a portion of another heated patient tube showing a helical heating element integrated on the surface thereof.
FIG. 5 is a perspective view of a portion of another heated patient tube showing a linear heating element integrated on the surface thereof.

The heating assembly 14 warms the fluid as it passes through the fluid passageway 26 and includes a heating element 28 and a connector 30. The heating element 28 may be embedded in the tube 12 substantially between the tube's inner and outer walls 18, 20 or attached or integrated on the outer wall 20. For example, FIG. 3 shows a tube 12A having an embedded heating element 28A, whereas FIGS. 4 and 5 show tubes 12B,C having outer heating elements 28B,C. The heating element 28 produces resistive-type heat when subjected to an electrical current or electromagnetic wave and may be a metal wire (e.g., a Nichrome wire), a metal filament, flexible ceramic strip, etched foil heater, or any other element that generates heat. Some embodiments of the heating element 28 may include a heat conductive layer such as teflon, kapton, silicone, or felt and an overlying insulating layer for protecting the heating element 28 and guiding heat from the heating element 28 to fluids carried in the fluid-carrying tube 12. In one embodiment, the heating assembly 14 doesn't just heat a small portion of the tube 12, but instead heats and maintains the temperature of the fluids along nearly the entire length of the tube 12. In another embodiment, the heating assembly 14 warms the fluids shortly after they enter the first end 22 of the tube 12 and maintains the temperature of the fluids before they exit the second end 24 of the tube 12.

The heating element 28 may encircle the interior fluid passageway in a coil (FIGS. 1 and 2), helical pattern (heating element 28A of FIG. 3 and heating element 28C of FIG. 5), longitudinal or lateral back-and-forth pattern, or any other suitable pattern, or may extend in a single parallel line (heating element 28B of FIG. 4). The pitch or density of the pattern may be selected to provide any desired amount of heating and may even be variable for providing concentrated heating along the length of the tube 12. For example, the density of the pattern may decrease from the first open end 22 of the tube toward the second open end 24 of the tube 12, to ensure fluids are quickly and uniformly heated as they enter the tube 12 but not overheated before they exit the tube 12. The heating element 28 may terminate any distance from the second end 24 of the tube, and in one embodiment, terminates between one inch and three inches before the second end 24.

In another embodiment, more than one heating element may be embedded in a single piece of tube. For example, a first heating element may be embedded in the tube 12 near its first open end 22 and a second heating element may be embedded in the tube near its second open end 24. This embodiment heats fluids as they first enter the tube 12 and then heats the fluids again, if necessary, as they exit the tube 12. The control assembly described below may provide different amounts of power to the heating elements so as to provide different levels of heating. For example, the control assembly may provide more power to the first heating element so as to quickly warm a refrigerated fluid and less power to the heating element so as to maintain the fluid temperature without overheating the fluid. Each heating element may may have its own connector or the heating elements may share a single connector.

The connector 30 extends at least partially from the outer wall 20 of the tube 12 so that it may be connected to a control assembly 100 (described below) or directly to a power source for powering the heating element 28. The connector 30 may be a USB connector, mini USB connector, 4-pin or 16-pin connector, 120 VAC connector, 12 VDC connector, or any other connector capable of providing electricity to the heating element 28. In some embodiments, the connector 30 may be omitted, and the heating element 28 may receive power inductively or through other wireless methods. The connector 30 may include separate electrical contacts, one or more for delivering electricity to the heating element 28 and one or more for receiving temperature data from a temperature sensor 16 described below. Alternatively, separate connectors may be used for powering the heating element 28, delivering data from the temperature sensor 16 to the control assembly 100 and/or controlling other components.

Alternatively, or in addition to the connector 30, the tube 12 may include an RF antenna 32 for wirelessly communicating with the control assembly 100. The RF antenna 32 may be embedded or extruded in the tube 12 substantially between the inner wall 18 and outer wall 20, mounted on the tube 12, or extending from the tube 12 for improved reception. The RF antenna 32 may be configured to transmit signals representative of a temperature of the heating element 28, a unique identifier of the heated patient tube assembly 10, or any other suitable information to a controller of the control assembly 100. The RF antenna 32 may also be configured to receive signals from the controller such as instructions to change an output level of the heating element 28.

The temperature sensor 16 senses a temperature of the tube 12, the fluid in the tube, and/or the heating element 28 and may be a thermistor, a thermocouple, a silicon bandgap temperature sensor, temperature sensing wire, or any other temperature sensor. The temperature sensing 16 may be mounted on the tube 12 as shown in FIG. 1, embedded in the tube 12 substantially between the tube's inner wall 18 and outer wall 20, or integrated in the heating element 28. The temperature sensor 16 may directly sense a temperature of the tube 12 or may calculate an estimated temperature as a function of a voltage drop across the heating element 28, a current draw across the heating element 28, or any other suitable electronic property. The temperature sensor 16 may provide temperature data to the controller via the connector 30 or wirelessly via radio frequency signal transmissions of the RF antenna 32, near frequency communication (NFC) technology, or the like.

The temperature sensor described and illustrated herein may be changed without departing from the scope of the invention. For example, additional temperature sensors and/or different types of temperature sensors may be used for more accurate temperate readings and more complete data collection. In one embodiment, several temperature sensors 16 may be positioned along the length of the tube for sensing temperatures at several locations. For example, a temperature sensor may be positioned near the first end 22 of the tube 12, and another temperature sensor may be positioned near the second end 24 of the tube 12 such that a temperature difference between the two opposite ends of the tube 12 may be sensed and used to determine a heating level of the heating element 28. In another embodiment, a sensor may be placed near the first open end 22 of the tube 12, another sensor may be placed near the second open 24 end of the tube 12, and at least one more sensor may be spaced between the other two sensors such that temperatures of the fluid may be sensed as the fluid travels through the entire length of the tube 12. When only one temperature sensor is provided, it is preferably positioned near the second end 24 of the tube 12 so as to sense a temperature of the fluid immediately before it is discharged from the tube 12.

Figure 6:
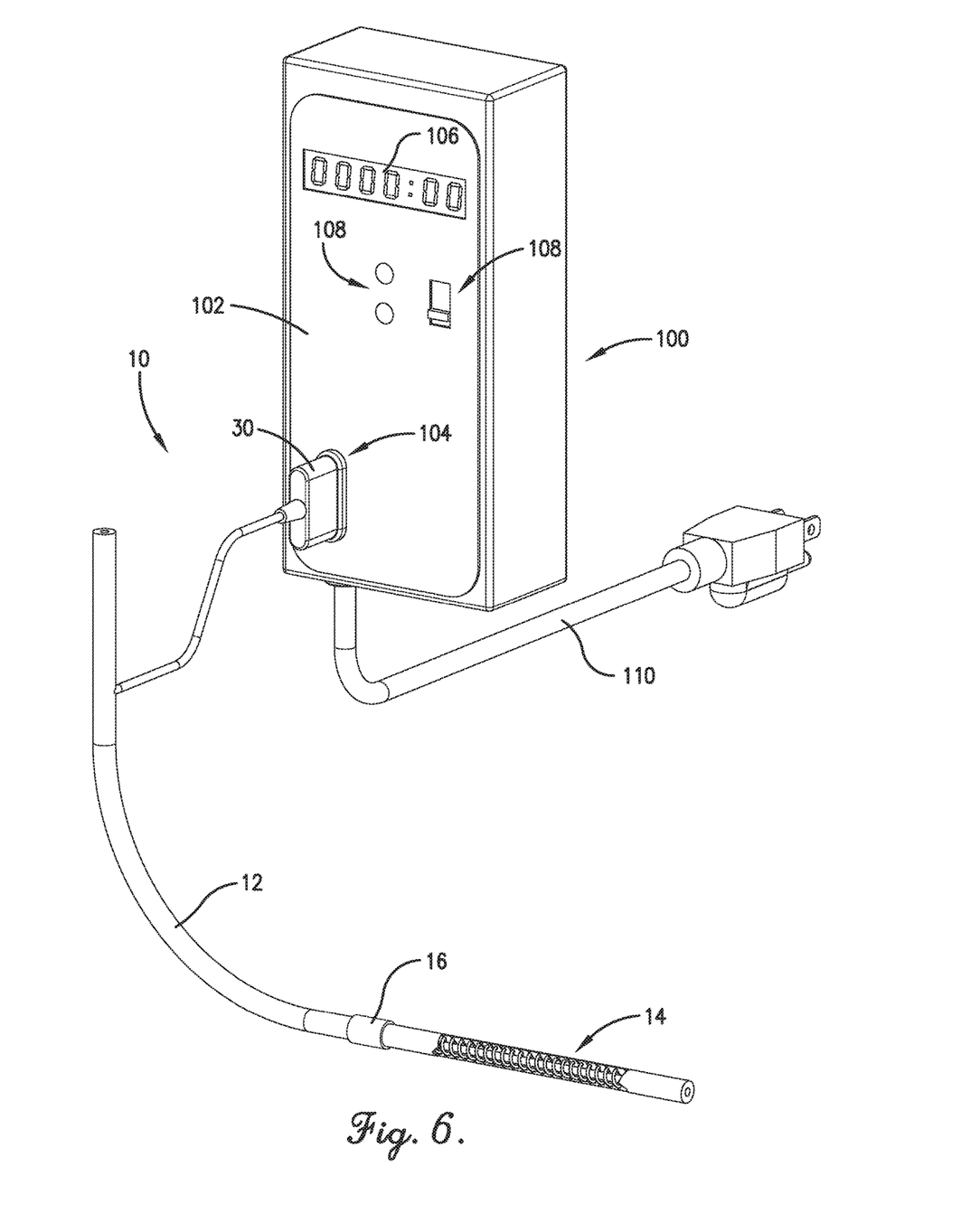
FIG. 6 is a perspective view of a control assembly connected to the heated patient tube assembly of FIG. 1.

Turning to FIG. 6, the control assembly 100 controls operation of the heating element 28 such that fluids exit the tube 12 at a desired and consistent temperature. The control assembly 100 is a separate system that provides power to the heating element 28 via the connector 30 in a first mode. An embodiment of the control assembly 100 comprises a controller 102 configured to be coupled with the temperature sensor or sensors 16 and the heating element 28 and is operable to control a temperature or power level of the heating element 28 in response to data from the temperature sensor 16. The controller 102 may include any combination of control circuitry, power circuitry, controllers, processors, and/or other electronics and has internal or external memory for storing the data and the computer programs described below.

The controller 102 may be mounted remotely from the tube 12 in its own enclosure and connected to the heating element 28 and the sensor 16 via the connector 30. In another embodiment, the controller 102 may be wired to a cable between the connector 30 and the heating element 28. In this embodiment, no external control of the patient tube assembly 10 is required, such that the connector 30 only requires a power source connection. The controller 102 and temperature sensor 16 may also be configured to communicate wirelessly such as via radio frequency signal transmissions of the RF antenna 32, near frequency communication (NFC) technology, or the like.

The controller 102 may implement aspects of the invention with one or more computer programs stored in or on computer-readable medium residing on or accessible by the controller. Each computer program preferably comprises an ordered listing of executable instructions for implementing logical functions in the controller. Each computer program can be embodied in any non-transitory computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can store the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

Figure 7:
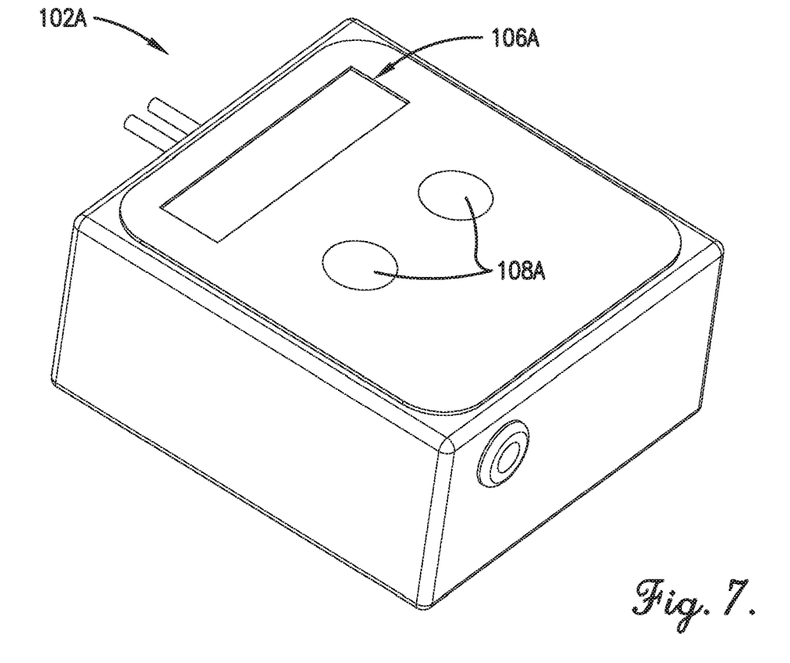
FIG. 7 is a front perspective view of a compact control assembly for use with the heated patient tube assembly of FIG. 1.
Figure 8:
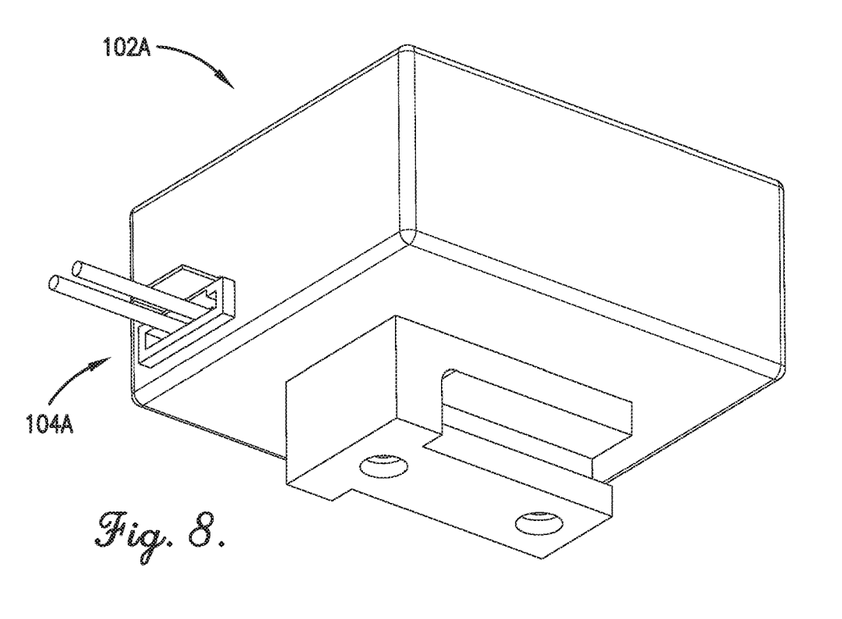
FIG. 8 is a rear perspective view of the compact control assembly of FIG. 7.

Embodiments of the controller 102 may further include a port 104 for connecting to the connector 30 extending from the tube 12, a display 106, a number of user inputs 108, and a power source 110, all of which may be contained within or on a housing as shown in FIG. 6. More details of such a controller are described in more detail in U.S. patent application Ser. No. 15/282,612, FLUID WARMING DEVICE, filed Sep. 30, 2016, hereby incorporated by reference into the present application in its entirety. In another embodiment, a compact controller 102A may have a standard or proprietary port 104A, a simplified readout display 106A and minimal controls 108A (e.g., power switch and temperature controls) as shown in FIGS. 7 and 8.

The above-described heated patient tube assembly 10 may be selectively used in any combination of three different modes: a first mode in which the heating element 28 is powered or activated via the connector 30, a second mode in which the heating element 28 is powered via induction, and a third mode in which the tube 12 is inserted into and heated by an external warming device. In all three modes, the first end 22 of the tube 12 is connected to a pump or other fluid source, and the opposite second end 24 of the tube is connected or otherwise provided to a patient.

In the first mode, the connector 30 extending from the tube 12 is coupled with the control assembly 100 or another power source. The pump draws fluid from the fluid source and may force it through the tube 12 at a flow rate of approximately 0.25 ml/min to approximately 1 ml/min. The fluid may also be gravity fed. The heating element 28 warms the tube 12 and fluids as the fluids pass through the tube.

The controller 102 maintains the temperature of the fluids within the tube between approximately 90° F. (32° C.) and 103° F. (39° C.). When the controller 102 determines via the temperature sensor 16 that the fluid-carrying tube or the fluids therein are above 103° F. (39° C.) or any other selected upper limit temperature, the controller 102 temporarily deactivates or reduces the output of the heating element 28 until the temperature has dropped to another predetermined temperature between 90° F. (32° C.) and 103° F. (39° C.). The controller 102 reactivates or increases the power of the heating element 28 when the temperature of the tube 12 drops to the predetermined lower threshold temperature or when the temperature of the tube drops to an intermediate temperature. This ensures that the temperature of the fluid exiting the tube 12 is within a thermo-neutral zone (TNZ) or another desired temperature range. The controller 102 may shut down the heating element 28 or generate a warning if the temperature of the tube 12 and/or fluids therein is near, at, or above 120° F. Temperatures this high may damage the tube 12 and may be harmful to the patient. Thus, the heated patient tube assembly 10 may have a maximum operating temperature of approximately 120° F.

The controller 102 may maintain the temperature of the fluids in the tube 12 by frequently activating and deactivating the heating element 28 when the tube reaches these temperatures. This allows the temperature of the tube, and hence the temperature of the fluid being delivered into the patient's vein, stomach, or intestine, to remain relatively constant during operation instead of rising and falling between the upper and lower threshold temperatures of the TNZ.

In the second mode, the connector 30 is left un-connected while the heating element 28 is powered via induction or other wireless power transfer means. For example, the tube 12 may be placed near an induction power source so as to induce a current in the heating element 28. The temperature of the fluids passing through the tube 12 may be maintained via the controller 102 or another external control device. To that end, the heating element 28 may receive control inputs via the RF antenna 32.

In the third mode, at least a portion of the tube 12 may be inserted into a warming device and heated by a heating element of the fluid warming device. For example, a portion of the tube 12 may be threaded into an elongated heating channel of a fluid warming device such that the fluid is warmed as it passes through the elongated heating channel. The temperature of the fluids passing through the tube 12 may be maintained via a controller of the fluid warming device.

Importantly, more than one mode or aspects of more than one mode may be used simultaneously. For example, the connector 30 may be coupled to the control assembly 100 for collecting or displaying temperature data and other information, while the heating element 28 is powered via the induction power source. Alternatively, the heated patient tube assembly 10 may be powered via the connector 30 while temperature data and other information is transmitted to the controller 102 of the control assembly 100 wirelessly via the RF antenna 32. In some instances, supplemental heat or power may be desired and provided from two or more sources. For example, the connector 30 may be coupled to the control assembly 100 and the tube 12 may be inserted into an external warming device such that the fluids are warmed via heat generated by the heating element 28 and heat generated by the external warming device. This may be useful when the tube 12 does not precisely fit the available external warming device and thus is not adequately heated by the external warming device. In a similar example, a portion of the tube 12 near its first end 22 may be inserted into the external warming device such that the external warming device provides initial heat for warming the fluids to a temperature in the TNZ while the heating element 28 maintains the temperature of the fluids as they pass through the tube 12.

The above-described heated patient tube assembly 10 provides several advantages. For example, the heated patient tube assembly 10 can be selectively operated in any combination of three different modes: the first mode in which the connector 30 is connected to a control assembly 100 or another power source, the second mode in which the heated patient tube assembly 10 is powered wirelessly, and the third mode in which the tube 12 is inserted into and heated by an external fluid warming device. More than one mode or aspects of more than one mode can be implemented simultaneously, which allows the heated patient tube assembly 10 to be used with a wide variety of control assemblies, power sources, and heating devices. This significantly reduces the risk that the heated patient tube assembly 10 is used with incompatible components and thus does not properly heat the fluids.

Figures 9, 10:
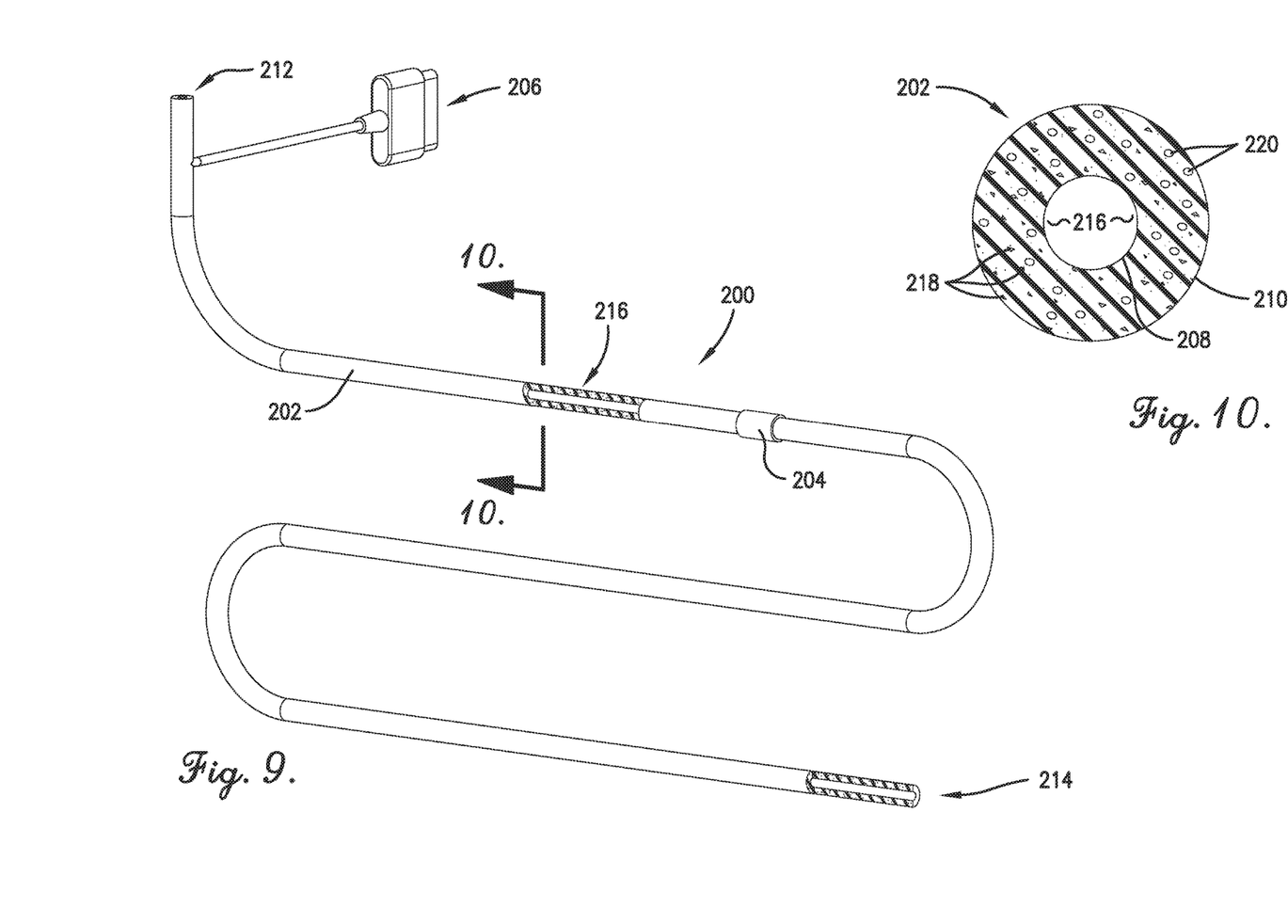
FIG. 9 is a perspective view of a heated patient tube assembly constructed in accordance with another embodiment of the invention with portions of the assembly shown in partial section to reveal internal components.
FIG. 10 is a vertical sectional view of the heated patient tube assembly of FIG. 9.

Another embodiment of the invention is a heated patient tube assembly 200 broadly comprising an elongated hollow tube 202, a temperature sensor 204, and a connector 206, as shown in FIGS. 9 and 10. The tube 202 has an inner wall 208, an outer wall 210, and first and second open ends 212, 214, with the inner wall 208 defining an interior fluid passageway 216 for carrying fluids, and a plurality of thermally conductive particles 218 and color changing particles 220 embedded in the tube 202. The first open end 212 receives fluids from a pump, bag, or other fluid source and the second open end 214 delivers the fluids to a patient, or vice versa. The tube 202 may have any length and diameter and is preferably constructed of medical grade rubber, plastic, or similar flexible materials.

The thermally conductive particles 218 warm the fluid as it passes through the fluid passageway 216 and are embedded in the tube 202 substantially between the tube's inner and outer walls 208, 210. The thermally conductive particles 218 produce resistive-type heat when subjected to an electrical current or electromagnetic wave and may be silicone, foil, copper, titanium, and/or silver particles or any other particles that transfer heat or generate heat under electric load. The thermally conductive particles 218 may be microparticles or even nanoparticles and may be layered or extruded between the inner wall 208 and outer wall 210. The thermally conductive particles 218 may be concentrated near the inner wall 208 such that heat is transferred primarily inwardly towards the fluids in the fluid passageway 216. The thermally conductive particles 218 may be evenly dispersed along the tube 202 or may be concentrated near the ends 212, 214 of the tube 202 for warming the fluids as they enter the fluid passageway 216 at the first end 212 and maintaining their temperature before they exit the fluid passageway 216 at the second end 214.

The color changing particles 220 indicate whether the temperature of the tube 202 is within a safe or desired range and are embedded in the tube 202 substantially between the tube's inner and outer walls 208, 210. For example, the color changing particles 220 may change from a first color to a second color to indicate that the temperature of the tube 202 is between 98° F. and 105° F. and may change from the first color or second color to a third color to indicate that the tube 202 is near or over 120° F. and that the tube 202 should be discarded. As discussed above, temperatures near or above 120° F. may damage the tube 202 and may be harmful to the patient. The color changing particles 220 may be any thermochromic material such as an ink, a dye, crystals, or fabric. In another embodiment, a band, tape, wrap, or other strip of color changing material may be positioned on or attached to the outer wall 210 of the tube 202.

The temperature sensor 204 may be mounted on the tube 202 or embedded in the tube 12 substantially between the tube's inner wall 208 and outer wall 210 and is substantially similar to the temperature sensor 16 described above. For example, the temperature sensor 204 may be a thermistor, a thermocouple, a silicon bandgap temperature sensor, or any other temperature sensor.

The connector 206 extends at least partially from the outer wall 210 of the tube 202 so that it may be connected to a control assembly or directly to a power source for providing electricity to the thermally conductive particles 218 and is substantially similar to the connector 30 described above.

The connector 206 may be a USB connector, mini USB connector, 4-pin or 16-pin connector, 120 VAC connector, 12 VDC connector, or any other connector capable of providing electricity to the thermally conductive particles 218. In some embodiments, the connector 206 may be omitted, and the thermally conductive particles 218 may receive power inductively or through other wireless methods. In another embodiment, the tube 202 may be inserted into a controller for triggering the thermally conductive particles 218, which eliminates the need for the connector 206.

The above-described heated patient tube assembly 200 provides several advantages. For example, the thermally conductive particles 218 may be embedded in the tube 202 and provide a more predictable and controllable heating profile along the tube 202. The thermally conductive particles 218 may also be concentrated near the inner wall 208, thus providing more efficient heat transfer to the fluids as they pass through the interior fluid passageway 216. The heated patient tube assembly 200 can be connected to a control assembly, powered and controlled wirelessly, and/or used with external heating devices.

Figures 11, 12:
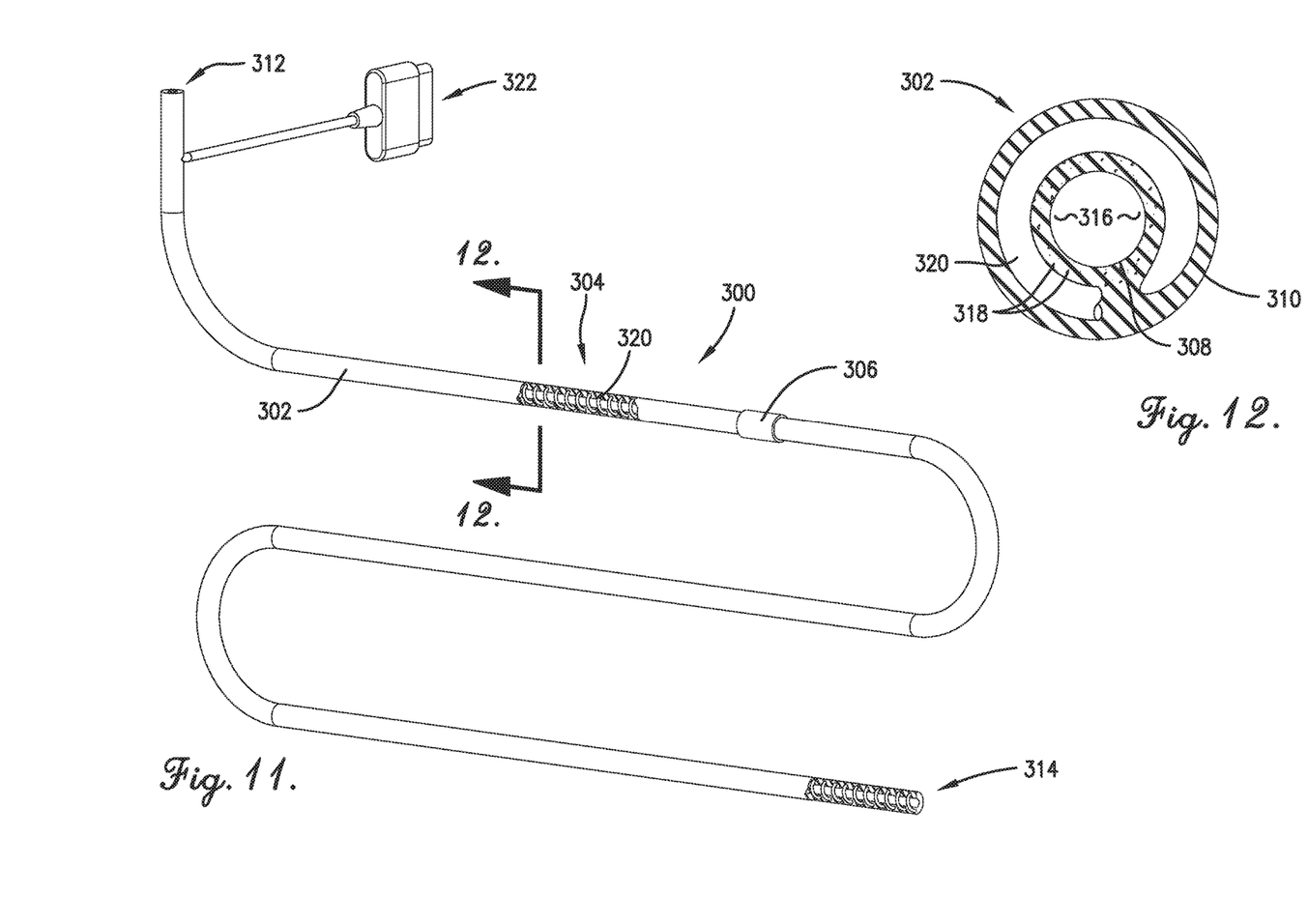
FIG. 11 is a perspective view of a heated patient tube assembly constructed in accordance with another embodiment of the invention with portions of the assembly shown in partial section to reveal internal components.
FIG. 12 is a vertical sectional view of the heated patient tube assembly of FIG. 11.

Another embodiment of the invention is a heated patient tube assembly 300 broadly comprising an elongated tube 302, a heating assembly 304, and a temperature sensor 306, as shown in FIGS. 11 and 12. The tube 302 has an inner wall 308, an outer wall 310, and first and second open ends 312, 314, with the inner wall 308 defining an interior fluid passageway 316 for carrying fluids and a plurality of thermally conductive particles 318 embedded between the inner wall 308 and outer wall 310. The tube 302 may be configured for use as an intravenous (IV) tube, an enteral feeding tube, a blood transfusion tube, and/or any other device for carrying IV fluids, milk, feeding formulas, blood, and/or any other fluids to infants, elderly person, or any other patients or persons. The first open end 312 receives fluids from a pump, bag, or other fluid source and the second open end 314 delivers the fluids to a patient, or vice versa. The tube 302 may have any length and diameter and is preferably constructed of medical grade rubber, plastic, or similar flexible materials.

The thermally conductive particles 318 transfer heat from a heating element of the heating assembly 304 to the fluid as it passes through the fluid passageway 316 and are embedded in the tube 302 substantially between the tube's inner wall 308 and the heating element of the heating assembly 304. The thermally conductive particles 318 may be silicone, foil, copper, titanium, and/or silver particles or any other thermally conductive particles. The thermally conductive particles 318 may be microparticles or even nanoparticles and may be layered or extruded between the inner wall 308 and the heating element. The thermally conductive particles 318 may be concentrated near the inner wall 308 such that heat is transferred primarily inwardly towards the fluids in the fluid passageway 316. The thermally conductive particles 318 may be evenly dispersed along the tube 302 or may be concentrated near the ends 312, 314 of the tube 302 for warming the fluids as they enter the fluid passageway 316 at the first end 312 and maintaining their temperature before they exit the fluid passageway 316 at the second end 314.

The heating assembly 304 includes a heating element 320 and a connector 322 and is substantially similar to the heating assembly 14 described above. For example, the heating element 320 may extend parallel to the tube's interior fluid passageway 316 in a relatively straight line or may encircle the interior fluid passageway in a helical pattern, longitudinal or lateral back-and-forth pattern, or any other suitable pattern. The pitch or density of the pattern may be selected to provide any desired amount of heating and may even be variable for providing concentrated heating along the length of the tube 302. For example, the density of the pattern may decrease from the first open end 312 of the tube toward the second open end 314 of the tube 302, to ensure fluids are quickly and uniformly heated as they enter the tube 302 but not overheated before they exit the tube 302. The heating element 320 may terminate any distance from the second end 314 of the tube, and in one embodiment, terminates between one inch and three inches before the second end 314.

The connector 322 extends at least partially from the outer wall 310 of the tube 302 so that it may be connected to a control assembly or directly to a power source for providing electricity to the heating element 320 and is substantially similar to the connectors 30, 206 described above. The connector 322 may be a USB connector, mini USB connector, 4-pin or 16-pin connector, 120 VAC connector, 12 VDC connector, or any other connector capable of providing electricity to the heating element 320. In at least one mode of use, the connector 322 may remain disconnected and the heating element 320 may receive power inductively or through other wireless methods.

The temperature sensor 306 is substantially similar to the temperature sensors 16, 204 described above. For example, the temperature sensor 306 may be a thermistor, a thermocouple, a silicon bandgap temperature sensor, or any other temperature sensor. The temperature sensor 306 may be mounted on the tube 302 or embedded in the tube 302 substantially between the tube's inner wall 308 and outer wall 310.

The above-described heated patient tube assembly 300 provides several advantages. For example, the thermally conductive particles 318 can be embedded in the tube 302 and provide a more predictable and controllable heating profile along the tube 302. The thermally conductive particles 318 may also be concentrated near the inner wall 308, thus providing more efficient heat transfer to the fluids as they pass through the interior fluid passageway 316. The heated patient tube assembly 300 can be connected to a control assembly, powered and controlled wirelessly, and/or used with external heating devices.

Although the invention has been described with reference to the embodiments illustrated in the attached drawing figures, it is noted that equivalents may be employed and substitutions made herein without departing from the scope of the invention as recited in the claims. It will be understood that elements and variations from the different embodiments described above can be used in combination.

Having thus described various embodiments of the invention, what is claimed as new and desired to be protected by Letters Patent includes the following:

1. A heated patient tube assembly comprising: an elongated hollow tube having—
    an inner wall and an outer wall, the inner wall defining an interior fluid passageway for carrying fluids,
    a first end configured to be connected to a pump or fluid source or receiving the fluids therefrom, and
    a second end opposite the first end for delivering the fluids to a patient; and
    a heating assembly including—
    a heating element embedded substantially between the inner wall and outer wall of the elongated hollow tube, the heating element being configured to receive an electric current via a wired connection and create an electric current when subjected to an electromagnetic field, the heating element having an electrical resistivity such that the heating element generates resistive heating from the received or induced electric current, the heating element being configured to transfer heat to the fluids as the fluids pass through the interior fluid passageway, and a connector configured to connect the heating element to a power source, the elongated hollow tube being configured to be selectively used simultaneously in at least two of three different modes: a first mode in which the heating element is powered via the connector, a second mode in which the heating element is powered via induction, and a third mode in which the tube is inserted into and warmed by a warming device.

2. The heated patient tube assembly of claim 1, further comprising an RF antenna embedded substantially between the inner wall and outer wall of the elongated hollow tube for at least one of wirelessly receiving data from a controller or wirelessly transmitting data to the controller.

3. The heated patient tube assembly of claim 2, wherein the RF antenna is configured to transmit a signal representative of a temperature of the heating element to the controller.

4. The heated patient tube assembly of claim 2, wherein the RF antenna is configured to transmit a signal representative of an identifier of the elongated hollow tube to the controller.

5. The heated patient tube assembly of claim 4, wherein the identifier is a unique identifier.

6. The heated patient tube assembly of claim 2, wherein the RF antenna is configured to receive a control signal for changing an output level of the heating element from the controller.

7. The heated patient tube assembly of claim 1, further comprising an RF antenna extruded in the elongated hollow tube for at least one of wirelessly receiving data from a controller or wirelessly transmitting data to the controller.

8. The heated patient tube assembly of claim 1, wherein the heating element is configured to heat the elongated hollow tube up to a maximum of 120° F.

9. The heated patient tube assembly of claim 1, further comprising a controller configured to temporarily deactivate or reduce the output level of the heating element until a temperature of the elongated hollow tube has dropped below an upper threshold temperature.

10. The heated patient tube assembly of claim 1, further comprising a controller configured to maintain a temperature of the fluids passing through the elongated hollow tube between approximately 90° F. and 103° F.

11. The heated patient tube assembly of claim 1, further comprising a controller configured to generate a warning if the elongated hollow tube is heated above 120° F.

12. A heated patient tube assembly comprising: an elongated hollow tube having—
an inner wall and an outer wall, the inner wall defining an interior fluid passageway for carrying fluids,
a first end configured to be connected to a pump or fluid source for receiving the fluids therefrom, and
a second end opposite the first end for delivering the fluids to a patient; a heating assembly including—
a heating element embedded substantially between the inner wall and outer wall of the hollow tube, the heating element being configured to receive an electric current via a wired connection and create an electric current when subjected to an electromagnetic field, the heating element having an electrical resistivity such that the heating element generates resistive heating from the received or induced electric current, the heating element being configured to transfer heat to the fluids as the fluids pass through the interior fluid passageway,
a temperature sensor integrated with the heating element for sensing a temperature of the heating element, and a connector configured to connect the heating element to a power source; and
an RF antenna embedded substantially between the inner wall and the outer wall of the hollow tube, the RF antenna being configured to wirelessly transmit a signal representative of a unique identifier of the heated patient tube assembly, a signal representative of a temperature of the heating element, and a signal representative of power usage of the heating element to a controller, and wirelessly receive a control signal for changing an output level of the heating element from the controller; the elongated hollow tube being configured to be selectively used simultaneously in at least two of three different modes: a first mode in which the heating element is powered via the connector, a second mode in which the heating element is powered via induction, and a third mode in which the hollow tube is inserted into and warmed by a warming device.

13. The heated patient tube assembly of claim 12, wherein the heating element is configured to heat the elongated hollow tube up to a maximum of 120° F.

14. The heated patient tube assembly of claim 12, wherein the controller is configured to temporarily deactivate or reduce the output level of the heating element until a temperature of the elongated hollow tube has dropped below an upper threshold temperature.

15. The heated patient tube assembly of claim 12, wherein the controller is configured to maintain a temperature of the fluids passing through the elongated hollow tube between approximately 90° F. and 103° F.

16. The heated patient tube assembly of claim 12, wherein the controller is configured to generate a warning if the elongated hollow tube is heated above 120° F.

* * * * *